March 26, 1974 A. BARBERET Plant Pat. 3,534
CARNATION PLANT
Filed Dec. 11 1972
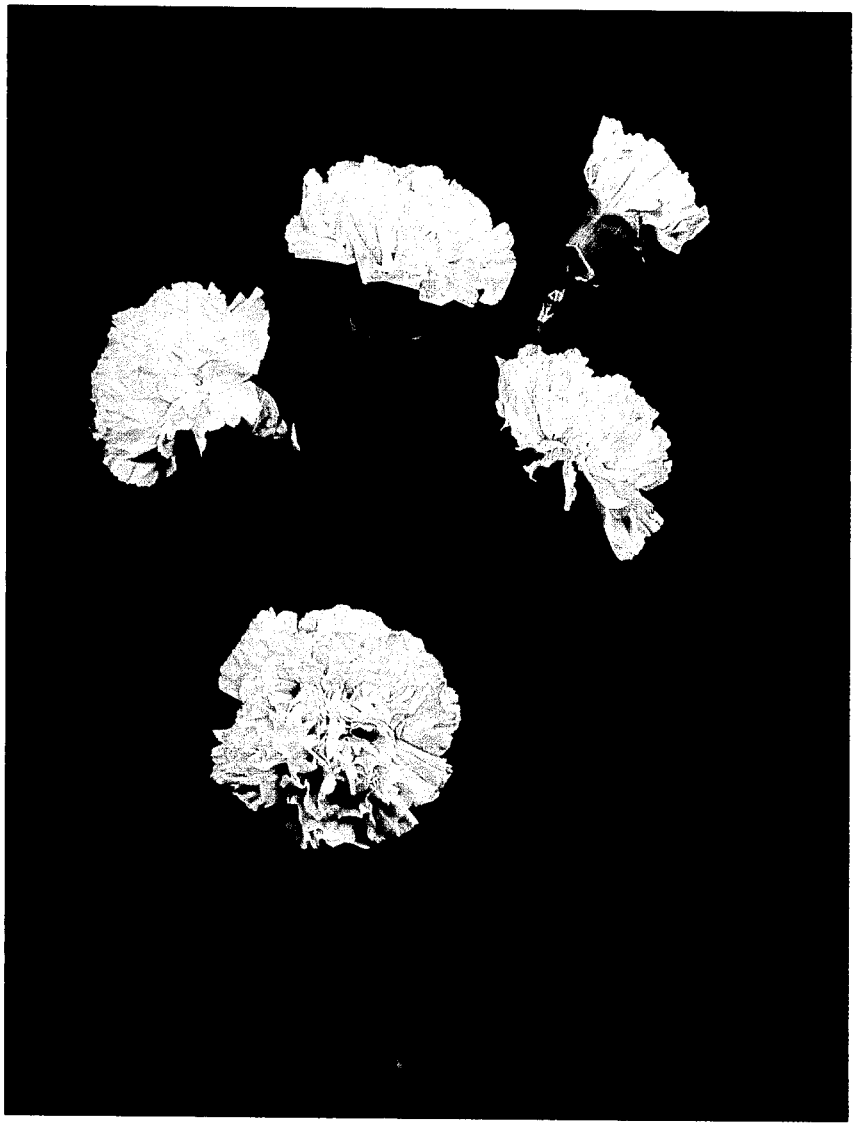

United States Patent Office

Plant Pat. 3,534
Patented Mar. 26, 1974

3,534
CARNATION PLANT

Alexandre Barberet, La Londe, France, assignor to Laboratoire de Physiologie Vegetale de La Londe, Societe Civile, La Londe, France Filed Dec. 11, 1972, Ser. No. 313,748
Claims priority, application Italy, Dec. 23, 1971, 32,847/71
Int. Cl. A01h *5/00*
U.S. Cl. Plt.—71 1 Claim

ABSTRACT OF THE DISCLOSURE

A new variety of carnation plant originated as a sport of the variety Barlo and distinguished by its continuous and profuse production of relatively large and very light ping colored flowers, the new plant having a vigorous and erect growth habit and the blooms having a favorable lasting quality both on the plant and as cut flowers.

BACKGROUND OF THE NEW PLANT

This new variety of carnation plant was discovered by me at Antibes, France, in 1969, among plants of the variety Barlo being grown for commercial production of cut flowers. The much paler pink coloring of the flower, compared with the parent variety, brought this sport to my attention and subsequent propagation of this sport by me, by means of cuttings, at Antibes, France, has shown this new plant to have its distinguishing characteristics firmly fixed and to hold true from generation to generation. Propagation of this new plant is now being done, by cuttings, at West Hartford, Conn., and in France.

DESCRIPTION OF THE DRAWINGS

My new variety of carnation plant is illustrated by the accompanying photographic drawings which show the form and color characteristics of the flower as nearly true as is reasonably possible to obtain by conventional photographic procedures.

DESCRIPTION OF THE NEW PLANT

The following is a detailed description of my new variety of carnation plant with color designations according to The Horticultural Colour Chart issued by the British Colour Council in collaboration with the Royal Horticultural Society at London, England.

*The plant*

Origin: Sport.
Parentage: Barlo (unpatented).
Classification:
*Botanic.—Dianthus caryophyllus.*
*Commercial.*—Carnation for cut flowers.
Form: Bush. The same as Sim types of carnation plants.
Height: About 60 cm.
Growth: Vigorous and erect, with normal upright branching.
Foliage: Quantity—abundant
*Leaf shape.*—Lanceolate and up to 16.2 cm. long.
*Texture.*—Smooth.
*Color.*—Upper side.—Leek Green 0085/1 and 2 to Carnation Green 00058 to 00058/1. Under side—Leek Green 0085/1 and 2 to Carnation Green 00058 to 00058/1
*Ribs.*—Single and axial.
*Petioles.*—None. Leaf is amplexicaul.

*The bud*

Form: Ovoid:
Size: Medium. Diameter: 23 mm.
Opening: Bud opens slowly.
Color: Light Green when sepals first divide and when petals begin to unfurl.
Sepals: Curl back.
*Color.*—Inside—Pale Green. Outside—Light Green.
Calyx: Large and pear shaped; rarely splits.
*Aspecis.*—Smooth.

*The flower*

Blooming habit: Continuous and profuse the year around.
Size of bloom: Medium, averaging 9.7 cm. in diameter and 5 cm. in depth.
Borne: Singly, after disbudding.
Shape: High center when bloom first opens, changing to globular as bloom matures.
Petalage: Number of petals—60 to 80, average about 70.
*Form.*—Fan shaped.
*Color.*—Venetian Pink 420/2 to 420/3 throughout the bloom.
*Appearance.*—Satiny.
Petaloids: About 10 in number.
*Size.*—About one-half the size of petals.
*Color.*—Pale Pink.
Persistence: Blooms hang on and dry.
Fragrance: Just perceptible.
Lasting quality:
*On plant.*—15 days.
*As cut flower.*—10 days.
Disease resistance: Plant resists *Fusarium coseum* as observed in areas where it has been grown.

*Reproductive organs*

Stamens:
*Anthers.*—About 10 in number, 2 to 3 mm. long.
*Filaments.*—2.5 cm. long. Color—White.
*Pollen.*—Yellowish in color.
Pistils.—2 or 3 in number. 4 cm. long.
*Stigmas.*—White and Pink in color.
Ovaries.—Cone shaped.

*Fruit*

Fertility: Slightly fertile.
Shape: Oblong.
Color: Greenish.

This new plant is particularly distinguished by the very pale pink color of its blooms, this coloration being substantially uniform throughout the bloom. This coloring is soft and lovely, much lighter than that of its parent, and is not affected by wet or hot weather remaining substantially the same throughout the life of the bloom. Otherwise this new plant has the general characteristics of its parent with respect to growth habit and continuous flowering.

I claim:

1. The new and distinct variety of carnation plant substantially as herein shown and described, characterized by the pale pink coloring of its blooms, when compared to the coloring of its parent, and by its very low splitting habit.

No references cited.

ROBERT E. BAGWILL, Primary Examiner